United States Patent
He

(10) Patent No.: US 8,175,710 B2
(45) Date of Patent: May 8, 2012

(54) STIMULATOR SYSTEM WITH ELECTRODE ARRAY AND THE METHOD OF MAKING THE SAME

(75) Inventor: Tom Xiaohai He, Simi Valley, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1037 days.

(21) Appl. No.: 11/375,638

(22) Filed: Mar. 14, 2006

(65) Prior Publication Data

US 2007/0219595 A1    Sep. 20, 2007

(51) Int. Cl.
*A61N 1/375* (2006.01)

(52) U.S. Cl. .......................................... 607/36; 607/37

(58) Field of Classification Search .................. 607/36, 607/116, 37
See application file for complete search history.

(56) References Cited

U.S. PATENT DOCUMENTS

| | | |
|---|---|---|
| 3,760,984 A | 9/1973 | Theeuwes |
| 3,845,770 A | 11/1974 | Theeuwes et al. |
| 3,916,899 A | 11/1975 | Theeuwes et al. |
| 3,923,426 A | 12/1975 | Theeuwes |
| 3,987,790 A | 10/1976 | Eckenhoff et al. |
| 3,995,631 A | 12/1976 | Higuchi et al. |
| 4,016,880 A | 4/1977 | Theeuwes et al. |
| 4,036,228 A | 7/1977 | Theeuwes |
| 4,111,202 A | 9/1978 | Theeuwes |
| 4,111,203 A | 9/1978 | Theeuwes |
| 4,203,440 A | 5/1980 | Theeuwes |
| 4,203,442 A | 5/1980 | Michaels |
| 4,210,139 A | 7/1980 | Higuchi |
| 4,256,115 A * | 3/1981 | Bilitch .............................. 607/9 |
| 4,327,725 A | 5/1982 | Cortese et al. |
| 4,360,019 A | 11/1982 | Portner et al. |
| 4,487,603 A | 12/1984 | Harris |
| 4,627,850 A | 12/1986 | Deters et al. |
| 4,692,147 A | 9/1987 | Duggan |
| 4,725,852 A | 2/1988 | Gamblin et al. |
| 4,865,845 A | 9/1989 | Eckenhoff et al. |
| 5,057,318 A | 10/1991 | Magruder et al. |
| 5,059,423 A | 10/1991 | Magruder et al. |
| 5,112,614 A | 5/1992 | Magruder et al. |
| 5,137,727 A | 8/1992 | Eckenhoff |

(Continued)

FOREIGN PATENT DOCUMENTS

WO    98/02209    1/1998

(Continued)

OTHER PUBLICATIONS

U.S. Appl. No. 11/040,209, filed Jan. 20, 2005 by Colvin et al., for "Implantable Microstimulator with Plastic Housing and Methods of Manufacture and Use" (Not Published).

(Continued)

*Primary Examiner* — Michael Kahelin

(74) *Attorney, Agent, or Firm* — Frommer Lawrence & Haug LLP; Patrick R. Turner

(57) ABSTRACT

An implantable microstimulator can include a housing with a surface containing a metal region. The housing defines an exterior and an interior. At least one conductive electrode is disposed on the exterior of the housing over the metal region of the housing. Adhesive is disposed between the metal region of the housing and the conductive electrodes. An electronic subassembly is disposed in the interior of the housing and coupled to the conductive electrodes through the housing.

20 Claims, 5 Drawing Sheets

U.S. PATENT DOCUMENTS

| | | | |
|---|---|---|---|
| 5,193,539 A | 3/1993 | Schulman et al. | |
| 5,193,540 A | 3/1993 | Schulman et al. | |
| 5,234,692 A | 8/1993 | Magruder et al. | |
| 5,234,693 A | 8/1993 | Magruder et al. | |
| 5,312,439 A | 5/1994 | Loeb | |
| 5,314,451 A | 5/1994 | Mulier | |
| 5,314,458 A | 5/1994 | Najafi et al. | |
| 5,328,087 A * | 7/1994 | Nelson et al. | 228/175 |
| 5,405,363 A | 4/1995 | Kroll et al. | |
| 5,405,367 A | 4/1995 | Schulman et al. | |
| 5,439,484 A * | 8/1995 | Mehra | 607/5 |
| 5,670,251 A * | 9/1997 | Difrancesco | 428/325 |
| 5,713,926 A * | 2/1998 | Hauser et al. | 607/5 |
| 5,728,396 A | 3/1998 | Peery et al. | |
| 5,782,891 A | 7/1998 | Hassler et al. | |
| 5,948,006 A | 9/1999 | Mann | |
| 6,024,704 A | 2/2000 | Meador et al. | |
| 6,051,017 A | 4/2000 | Loeb et al. | |
| 6,061,596 A | 5/2000 | Richmond et al. | |
| 6,164,284 A | 12/2000 | Schulman et al. | |
| 6,175,764 B1 | 1/2001 | Loeb et al. | |
| 6,181,965 B1 | 1/2001 | Loeb et al. | |
| 6,185,452 B1 | 2/2001 | Schulman et al. | |
| 6,185,455 B1 | 2/2001 | Loeb et al. | |
| 6,208,894 B1 | 3/2001 | Schulman et al. | |
| 6,214,032 B1 | 4/2001 | Loeb et al. | |
| 6,234,973 B1 | 5/2001 | Meador et al. | |
| 6,315,721 B2 | 11/2001 | Schulman et al. | |
| 6,368,315 B1 | 4/2002 | Gillis et al. | |
| 6,424,234 B1 | 7/2002 | Stevenson | |
| 6,498,043 B1 | 12/2002 | Schulman et al. | |
| 6,609,032 B1 | 8/2003 | Woods et al. | |
| 6,622,048 B1 | 9/2003 | Mann et al. | |
| 6,662,035 B2 | 12/2003 | Sochor | |
| 7,110,819 B1 * | 9/2006 | O'Hara | 607/36 |
| 7,483,746 B2 * | 1/2009 | Lee et al. | 607/40 |
| 7,647,109 B2 * | 1/2010 | Hastings et al. | 607/32 |
| 2002/0072778 A1 | 6/2002 | Guck et al. | |
| 2003/0236558 A1 | 12/2003 | Whitehurst et al. | |
| 2004/0034394 A1 | 2/2004 | Woods et al. | |
| 2004/0059392 A1 | 3/2004 | Parramon et al. | |
| 2004/0088032 A1 * | 5/2004 | Haller et al. | 607/116 |
| 2004/0147992 A1 | 7/2004 | Bluger et al. | |
| 2004/0220632 A1 | 11/2004 | Burnes | |

FOREIGN PATENT DOCUMENTS

| | | |
|---|---|---|
| WO | WO 98/37926 | 9/1998 |
| WO | WO 98/43700 | 10/1998 |
| WO | WO 98/43701 | 10/1998 |

OTHER PUBLICATIONS

U.S. Appl. No. 11/056,762, filed Feb. 11, 2005 by Tom He, for "An Impantable Microstimulator Having a Separate Battery Unit and Methods of Use Thereof" (Not Published).

Medtronic, "New Diagnostic Tool—Reveal? Insertable Loop Recorder" http://www.medtronic.com/reveal/new.html, prior to Mar. 31, 2006.

* cited by examiner

STIMULATOR SYSTEM WITH ELECTRODE ARRAY AND THE METHOD OF MAKING THE SAME

FIELD

The invention is directed to implantable microstimulators with one or more external electrodes and methods of manufacturing and using the devices. In addition, the invention is directed to implantable microstimulators having one or more conductive electrodes attached to a metal region of the microstimulator housing using an adhesive, and methods of manufacturing and using the devices.

BACKGROUND OF THE INVENTION

Implantable microstimulators have been developed to provide therapy for a variety of disorders, as well as other treatments. For example, implantable microstimulators can be used in neurological therapy by stimulating nerves or muscles, for urinary urge incontinence by stimulating nerve fibers proximal to the pudendal nerves of the pelvic floor, for erectile and other sexual dysfunctions by stimulating the cavernous nerve(s), for reduction of pressure sores or venous stasis, etc.

Implantable microstimulators, such as the BION® device (available from Advanced Bionics Corporation, Sylmar, Calif.), have exposed electrodes and a small, often cylindrical, housing that contains the electronic circuitry and power source that produce electrical pulses at the electrodes for stimulation of the neighboring tissues. It is preferable that the electronic circuitry and power source be held within the housing in a hermetically-sealed environment for the protection of the user and the protection of the circuitry and power source. Once implanted, it is often preferable that the microstimulator can be controlled and/or that the electrical source can be charged without removing the microstimulator from the implanted environment.

BRIEF SUMMARY OF THE INVENTION

In one embodiment, an implantable microstimulator includes a housing with a surface with a metal region. The housing defines an exterior and an interior. At least one conductive electrode is disposed on the exterior of the housing over the metal region of the housing. Adhesive is disposed between the metal region of the housing and the conductive electrodes. An electronic subassembly is disposed in the interior of the housing and coupled to the conductive electrodes through the housing.

In another embodiment, a method of making an implantable microstimulator includes disposing an electronic subassembly in a housing. The housing has a surface with a metal region and defines an exterior and an interior. Conductive electrodes are attached to the metal region on the exterior of the housing using an adhesive. The electronic subassembly is coupled to the conductive electrodes through the housing.

In another embodiment of the invention, a method of using an implantable microstimulator includes implanting an implantable microstimulator. The microstimulator includes a housing having an exterior surface with a metal region. The housing defines an exterior and an interior. At least one conductive electrode is disposed over the metal region of the housing. Adhesive is disposed between the metal region of the housing and the conductive electrodes. An electronic subassembly is disposed in the interior of the housing and coupled to the conductive electrodes. An electrical signal is provided to the conductive electrodes to stimulate a tissue.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION OF THE INVENTION

Figure 1:
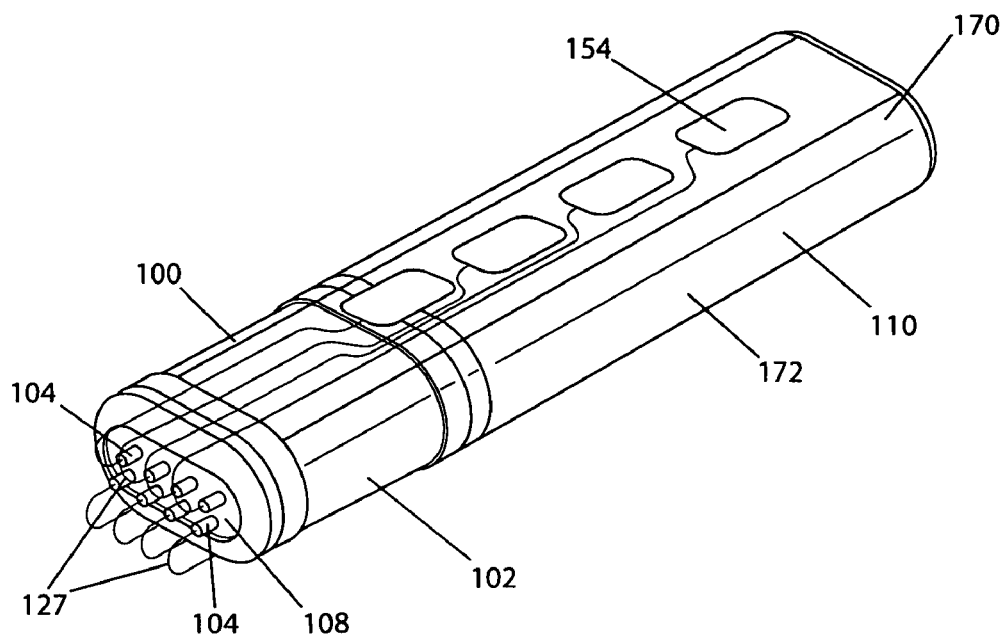
FIG. 1 is a schematic perspective view of one embodiment of a microstimulator, according to the invention.

The invention is directed to implantable microstimulators with one or more external electrodes and methods of manufacturing and using the devices. In addition, the invention is directed to implantable microstimulators having one or more conductive electrodes attached to a metal region of the microstimulator housing using an adhesive, and methods of manufacturing and using the devices.

Previously, implantable microstimulators have been made with electrodes disposed at the end(s) of a housing. Examples of such microstimulators are found in U.S. Pat. Nos. 5,193,539; 5,193,540; 5,312,439; 6,051,017; and 6,609,032; U.S. Patent Application Publication No. 2004/059392; U.S. patent application Ser. Nos. 11/040,209 and 11/056,762; and PCT Patent Application Publication Nos. 98/37926; 98/43700; and 98/43701, all of which are incorporated herein by reference.

In at least some applications, it is desirable that an implantable microstimulator be non-intrusive. It is often advantageous that the electrodes of the implantable microstimulator be located on the outside of the microstimulator housing. In at least some applications, the electrodes may be attached to the outside of the microstimulator housing using an adhesive. Preferably, the adhesive insulates the electrode from conductive regions of the housing if needed.

Several concerns are associated with using an adhesive to attach electrodes to a microstimulator housing. It may be difficult to apply the adhesive, which is often in the form of a liquid or paste, in a layer of uniform thickness so that there is uniform separation between the electrode surface and the surface of the microstimulator housing. When the electrode is not parallel to a metal or conductive region of the microstimulator housing, there may be shorting between the electrode and the microstimulator housing. Application of an adhesive may also result in contact of the adhesive with the external face of the electrode (that is, the side of the electrode that faces away from the microstimulator housing and toward the tissue). During the process of placing the adhesive between the microstimulator housing and the electrode(s), the adhesive may squeeze out from between the electrode and microstimulator housing, which may create an uneven surface, affect the appearance of the microstimulator, and/or affect the microstimulator or effective electrode dimensions. In addition, adhesive may cover parts of the electrode surface, changing the desired stimulation pattern. Because adhesive may be able to adhere to any object before it cures, it may be difficult, time-consuming or expensive to use tooling to align and fix the electrode(s) in place.

In at least some embodiments, one or more electrodes are attached to a metal region of a microstimulator housing using an adhesive. In one embodiment, the adhesive is non-conductive and is disposed in a layer of a substantially uniform thickness. The adhesive attaches the electrode to the metal region of the housing and insulates the electrode from the conductive regions of the housing.

Figure 2:
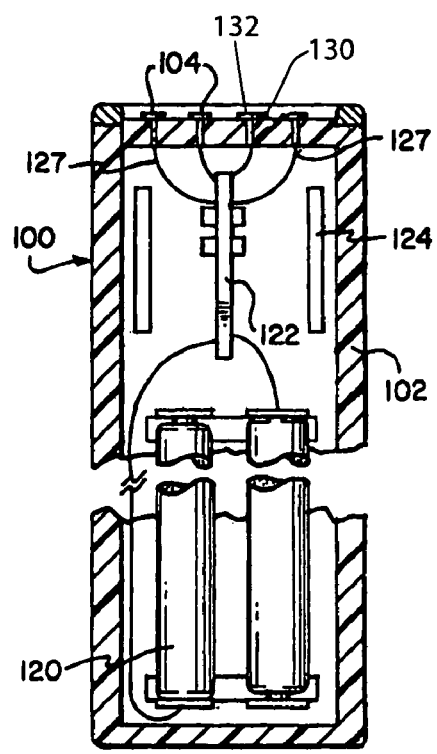
FIG. 2 is a schematic cross-sectional view of the interior of the microstimulator of FIG. 1.

FIGS. 1 and 2 illustrate one embodiment of an implantable microstimulator 100. The implantable microstimulator includes a housing 102, a power source 120, an electronic subassembly 122, an optional antenna 124, one or more conductive vias 104 extending through the housing 102 to couple the electronic subassembly 122 to electrodes 154 disposed on the exterior of the housing 102, one or more conductors 127 extending from the electronic subassembly 122 to the conductive via(s) 104 and from the conductive via(s) 104 to the electrode(s) 154. Other embodiments of an implantable microstimulator may include more or fewer components. It will be understood that the power source 120, components of the electronic subassembly 122, and/or the optional antenna 124 can be provided outside of the housing in a separate unit and coupled to the implantable microstimulator by a lead. Examples of such arrangements are described in U.S. patent application Ser. No. 11/056,762, incorporated herein by reference.

The housing 102 can be formed of any material that resists the transport of moisture into the interior of the housing and is sufficiently sturdy to protect the components in the interior of the housing from damage under expected implantation and usage conditions. At least the portion 108 of the housing 102 adjacent to the vias 104 is non-conductive. Suitable materials for the housing 102 (or a portion of the housing) include, for example, metals, ceramics, glass, and plastics. The housing of the microstimulator may advantageously be composed of biocompatible materials. The housing has a surface with at least one metal region 110. Suitable materials for the metal region 110 of the housing include, for example, platinum, iridium, tantalum, titanium, titanium nitride, niobium, including alloys of these or other metals. Metallic and ceramic portions of the housing can be coupled together by any suitable process including brazing.

The shape of the microstimulator housing 102 may be determined or influenced by the structure of the desired target, the surrounding area, and the method of implantation. The housing can have any shape including, for example, cylindrical, spherical, parallelepiped, cubic, and the like. In at least some embodiments, a non-cylindrical shape (for example, a parallelepiped shape) is preferred. The non-cylindrical shape can aid a practitioner in positioning the microstimulator correctly in relation to the tissue to be stimulated. In some embodiments, the shape has sides which are distinguishable based on at least one dimension. In the illustrated embodiment of FIGS. 1 and 2, the housing 102 has a roughly parallelepiped shape with two opposing sides 170 that are wider than two adjacent sides 172. This difference in dimension can aid the practitioner implanting the device in correctly positioning the microstimulator relative to the tissues to be stimulated. For example, as illustrated in FIG. 1, the electrodes 154 can be disposed on the wider side(s) 170 so that the practitioner can identify which side (for example, one of the wider sides) should be positioned adjacent the tissues to be stimulated. In one embodiment, electrodes 154 are provided on both of the wider sides 170 of the housing 102 so that a practitioner does not need to identify which of the two sides has electrodes. This can facilitate quicker implantation of the device into the patient. The parallepiped shape also yields more volume inside the implant with the same thickness, compared to a cylindrical shape.

In one embodiment, the housing 102 has a first end, a second end and a side wall between the first end and the second end. In one embodiment, the conductive electrode or electrodes 154 are located on the side wall of the housing, and not on the first end or the second end of the housing.

The lateral width of a side of the housing can be the same or can vary along the length of the housing. The width of a side can be, for example, no greater than 5 mm, no greater than 4 mm, no greater than 3.3 mm, or no greater than 3 mm. This width can be in the range of from, for example, 1 to 5 mm. It will be recognized that larger housings may be used for some applications.

In at least some embodiments, the length of the microstimulator is no greater than 30 mm. Typically the length of the microstimulator is in the range of 10 to 30 mm.

Optionally, the housing 102 can be covered, in full or in part, with a coating. The coating can be provided to improve or alter one or more properties of the housing including, for example, biocompatibility, hydrophobicity, conductivity, moisture permeability, leaching of material into or out of the housing, and the like. The optional coating can be a polymer material, inorganic material, or organic material. As an example, a silicone coating may be used to improve biocompatibility. In yet another example, a coating can be applied which contains a compound, such as, for example, a drug, prodrug, hormone, or other bioactive molecule, that can be released over time when the microstimulator is implanted.

The one or more conductive vias 104 are provided through a non-conductive portion 108 of the housing 102. In at least some embodiments, there are at least two conductive vias 104, but there can be any number of vias including two, four, six, eight, ten, or more conductive vias. The conductive vias 104 can all be formed through a single side of the housing 102, as illustrated in FIGS. 1 and 2 or vias can be formed through two or more sides of the housing. The vias 104 are typically filled with a conductive material such as a metal (including alloys). The vias 104 are used to couple the electrodes 154 to the electronic subassembly 122 which provides the stimulation signals to the electrodes 154.

In the illustrated embodiment, each via 104 includes a channel 130 through the housing and a capture pad or a conductive pin 132 disposed on the surface of the housing 102. In one example of forming the vias, a non-conductive plate (e.g., a ceramic plate) is provided with holes through the plate. For example, the holes can be provided in the plate by molding them in the plate or drilling the plate. The holes are filled with metal or other conductive material to form the channels of the via. For example, a platinum (or other metal) paste can be disposed in holes of a green state ceramic plate and then the plate and paste can be fired or a platinum pin can be brazed in place with gold applying high temperatures. In some instances, firing the ceramic plate may alter the position of the vias slightly.

In one example of forming the capture pads 132, a metal layer can be disposed on a surface of the plate and then the metal layer can be patterned using conventional techniques to form the capture pads 132. For example, a metal layer can be sputtered, or otherwise deposited using methods such as physical vapor deposition, chemical vapor deposition, electroplating, and electroless plating, onto the surface of the plate. The metal layer can be selectively etched to form the capture pads.

The electrodes 154 (see FIG. 1) typically form the anode and cathode of the microstimulator. The electronic subassembly 122 may be configured to allow each individual electrode to selectably operate as an anode or cathode or some electrodes may be designated as operable as cathodes only and other electrodes designated as operable as anodes only. In addition, the electronic subassembly 122 may be configured to allow multiple anodes and/or cathodes or may be configured to allow only one electrode to be an anode and one electrode to be a cathode at any given time.

In at least some embodiments, electrodes 154 may be disposed on only one side of the microstimulator housing 102. Alternatively, electrodes 154 may be disposed on more than one side of the microstimulator housing 102. At least one electrode is located on a metal region 110 of the housing 102 of the microstimulator. If the location of the electrodes is not readily apparent, the side of the housing 102 on which the electrode or electrodes 154 are disposed may be identified so the microstimulator can be implanted such that the electrode(s) lie adjacent to the tissues to be stimulated.

The electrodes 154 and conductors 127 can be formed using any conductive material. Examples of suitable materials include, for example, metals, alloys, conductive polymers, and conductive carbon.

In one embodiment, the electrode(s) 154 are of a thickness of from about 0.0005 inches (about 0.001 cm) to about 0.005 inches (about 0.01 cm). In another embodiment, the electrode(s) 154 are of a thickness of from about 0.001 inches (about 0.002 cm) to about 0.003 inches (about 0.008 cm). It will be recognized that thicker or thinner electrodes 154 may also be used.

An adhesive 140 (see FIG. 3) is disposed between the metal region 110 of the housing 102 and the conductive electrode(s) 154. The adhesive 140 may be any material that is suitable for attaching a conductive electrode 154 to a metal region 110 of the microstimulator housing 102. Generally, the adhesive is non-conductive. Suitable adhesives include, for example, silicones, epoxies, acrylics or any other implantable grade adhesives. In one embodiment, the adhesive 140 is an epoxy. Preferably, the adhesive 140 is biocompatible and will maintain a bond between the housing and electrode for at least the expected duration of implantation of the microstimulator.

In one embodiment, a layer of adhesive 140 is applied in a manner that prevents or reduces the occurrence of shorting between the metal region 110 of the housing 102 and the electrode(s) 154. Preferably, the layer of adhesive 140 between the electrode(s) 154 and the metal region(s) 110 of the housing 102 is of a substantially uniform thickness. For example, a layer of adhesive of a substantially uniform thickness is a layer that varies in thickness by no more than 30% over a region of interest. Alternatively, a layer of adhesive of a substantially uniform thickness is a layer that varies in thickness by no more than 20% or by no more than 10% over a region of interest. In one embodiment, the region of interest is the area of the electrode 154 that is in contact with the metal region 110 of the housing 102.

Figure 3:
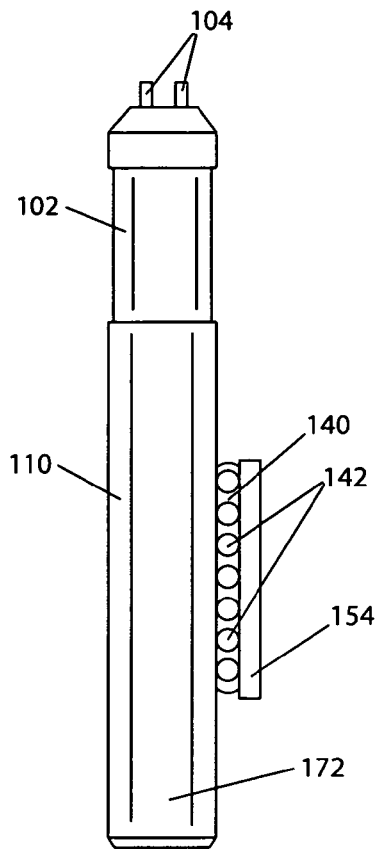
FIG. 3 is a schematic perspective view of one embodiment of a microstimulator with an electrode attached to the housing of the microstimulator by an adhesive containing spacer particles, according to the invention.

In one embodiment, the adhesive 140 comprises a plurality of spacer particles 142 (see FIG. 3). The spacer particles 142 may be any substance that facilitates the establishment and maintenance of a substantially uniform thickness of adhesive 140 between the metal region 110 of the housing and the electrode(s) 154. The spacer particles 142 may have any shape, and may be, for example, spheres, cubes, or irregularly shaped. In one embodiment, the spacer particles 142 are substantially spherical. Preferably, the spacer particles 142 have a diameter that is about equal to the desired thickness of the layer of adhesive 140. In one embodiment, the spacer particles 142 have a size ranging from about 0.00005 inches (about 0.0001 cm) to about 0.001 inches (about 0.003 cm). Suitable material for the spacer particles 142 include, for example, glass, silica, silica dust, synthetic resin, and suitable plastic material such as polyamide resin, polycarbonate resin and Teflon™. In one embodiment, the spacer particles 142 are of a substantially uniform diameter. The spacer particles 142 may be rigid or may be compressible. The spacer particle 142 may have a color that, in the transparent adhesive, can give an indication of uniform distribution within the adhesive.

In one embodiment, a conductor or conductors 127 couple the electrode(s) 154 to the electronic assembly 122 (see FIG. 1). Typically, the conductors 127 are insulated by an insulating material, except for the portion of the conductor 127 attached to the electrode 154, electronic subassembly 122, or other components of the electronic circuitry. The insulating material may be any material that is a poor conductor of an electrical signal, including, for example, Teflon™, non-conductive polymers, or metal oxidation that is poor in electrical conductivity.

Returning to FIG. 2, a power source 120 can be disposed within the housing 102. Any power source can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 124 or a secondary antenna. The external power source can be in a device that is mounted on the skin of the user or in a unit that is provided near the microstimulator user on a permanent or periodic basis.

If the power source 120 is a rechargeable battery, the battery may be recharged using the optional antenna 124, if desired. Power can be provided to the battery 120 for recharging by inductively coupling the battery through the antenna to a recharging unit 210 (see FIG. 4) external to the user. Examples of such arrangements can be found in the microstimulator references identified above.

Figure 4:
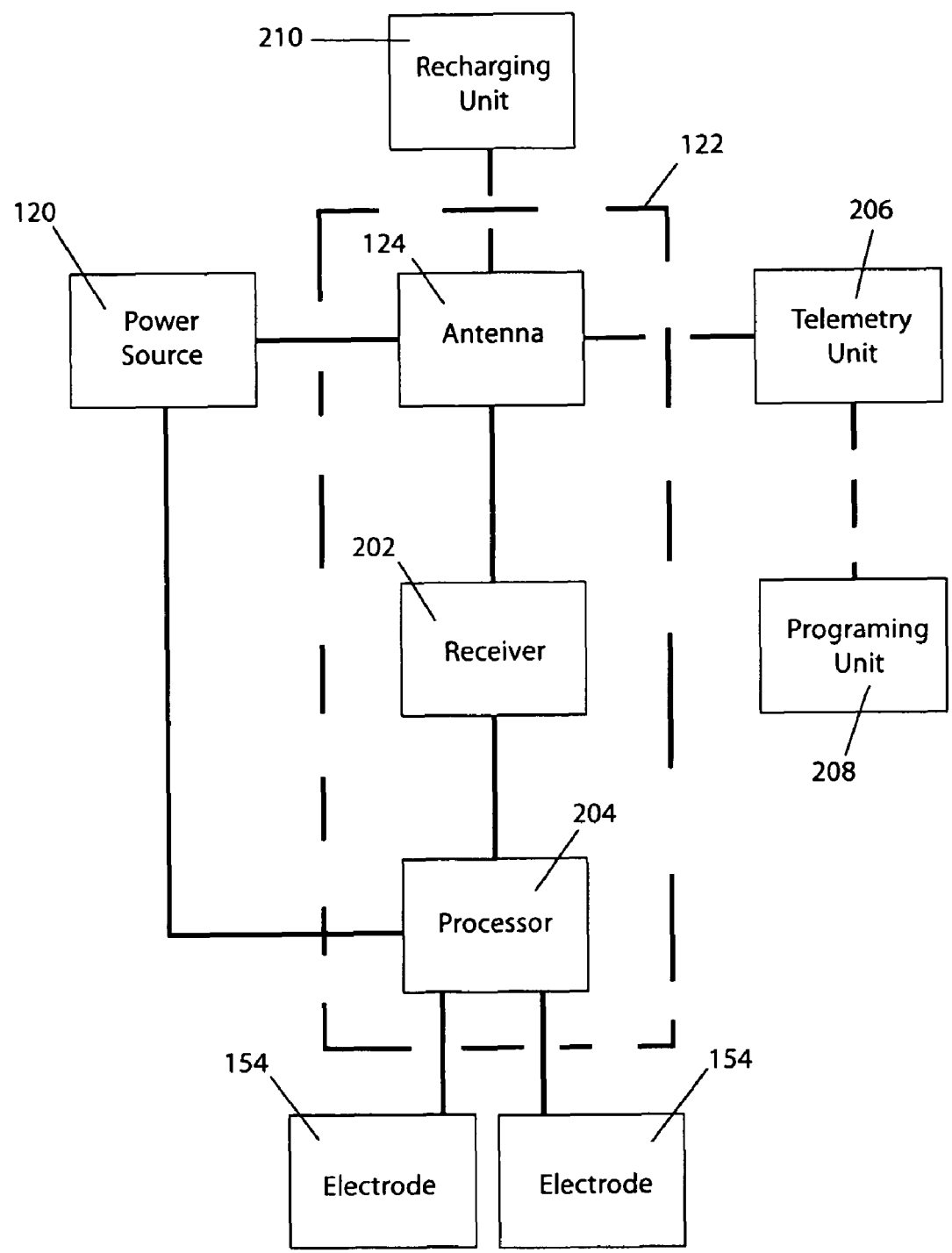
FIG. 4 is a schematic overview of one embodiment of components of a system for microstimulation of body tissue, according to the invention.

In one embodiment, electrical current is emitted by the electrodes 154 to stimulate motor nerve fibers, muscle fibers, or other body cells or tissues near the microstimulator. The electronic subassembly 122 provides the electronics used to operate the microstimulator and generate the electrical pulses at the electrodes 154 to produce stimulation of the body cells or tissues. FIG. 4 illustrates one embodiment of components of the electronic subassembly and associated units. It will be understood that the electronic subassembly can include more, fewer, or different components and can have a variety of different configurations including those configurations disclosed in the microstimulator references cited above. Some or all of the components of the electronic subassembly can be positioned on one or more circuit boards or similar carriers within the housing, if desired.

In the illustrated embodiment, a processor 204 is provided to control the timing and electrical characteristics of the microstimulator. For example, the processor can, if desired, control one or more of the timing, frequency, strength, duration, and waveform of the pulses. In addition, the processor 204 can select which electrodes can be used to provide stimulation, if desired. In some embodiments, the processor may select which electrode(s) are cathodes and which electrode(s) are anodes. In some embodiments with electrodes disposed on two or more sides of the housing, the processor may be used to identify which electrodes provide the most useful stimulation of the desired tissue. This process may be performed using an external programming unit, as described below, that is in communication with the processor 204.

Any processor can be used and can be as simple as an electronic device that produces pulses at a regular interval or the processor can be capable of receiving and interpreting instructions from an external programming unit 208 that allow modification of pulse characteristics. In the illustrated embodiment, the processor 204 is coupled to a receiver 202 which, in turn, is coupled to the optional antenna 124. This allows the processor to receive instructions from an external source to direct the pulse characteristics and the selection of electrodes, if desired.

In one embodiment, the antenna 124 is capable of receiving signals (e.g., RF signals) from an external telemetry unit 206 which is programmed by a programming unit 208. The programming unit 208 can be external to, or part of, the telemetry unit 206. The telemetry unit 206 can be a device that is worn on the skin of the user or can be carried by the user and can have a form similar to a pager or cellular phone, if desired. As another alternative, the telemetry unit may not be worn or carried by the user but may only be available at a home station or at a clinician's office. The programming unit 208 can be any unit that can provide information to the telemetry unit for transmission to the implanted microstimulator. The programming unit 208 can be part of the telemetry unit 206 or can provide signals or information to the telemetry unit via a wireless or wired connection. One example of a suitable programming unit is a computer operated by the user or clinician to send signals to the telemetry unit.

The signals sent to the processor 204 via the antenna 124 and receiver 202 can be used to modify or otherwise direct the operation of the microstimulator. For example, the signals may be used to modify the pulses of the microstimulator such as modifying one or more of pulse duration, pulse frequency, pulse waveform, and pulse strength. The signals may also direct the microstimulator to cease operation or to start operation or to start charging the battery.

Optionally, the microstimulator may include a transmitter (not shown) coupled to the processor and antenna for transmitting signals back to the telemetry unit 206 or another unit capable of receiving the signals. For example, the microstimulator may transmit signals indicating whether the microstimulator is operating properly or not or indicating when the battery needs to be charged. The processor may also be capable of transmitting information about the pulse characteristics so that a user or clinician can determine or verify the characteristics. The optional antenna 124 can have any form.

In one embodiment, the antenna comprises a coiled wire that is wrapped at least partially around the electronic subassembly within or on the housing.

Any method of manufacture of the microstimulator can be used. For example, the electronic subassembly, power source, and antenna can be manufactured as described in U.S. Patent Application Publication No. 2004/0059392. These components can then be placed inside the housing (or, alternatively, the housing can be formed, e.g., molded, around the components). The electrodes 154, as well as the vias 104 in the housing 102, can be formed as described above. Coatings on the electrodes or housing, if any, can be applied at appropriate points during the manufacturing process.

In one embodiment, a method of making an implantable microstimulator includes disposing an electronic assembly 122 in a housing 102, attaching at least one conductive electrode 154 to a metal region of the housing 102, and coupling the electronic assembly 122 to at least one electrode 154 through the housing 102. The method may further include coupling at least one conductive via 104 to the conductive electrode(s) 154. For example, a conductor(s) 127 may couple the conductive via(s) 104 to the conductive electrode(s) 154.

As one example of this method of manufacture, at least one conductive electrode 154 is disposed onto a mold 230 and adhesive 140 is applied to the conductive electrode(s) 154. The adhesive 140 may be applied using any method including, for example, spray coating, brush coating, programmed dispensing, and the like.

Figure 5:
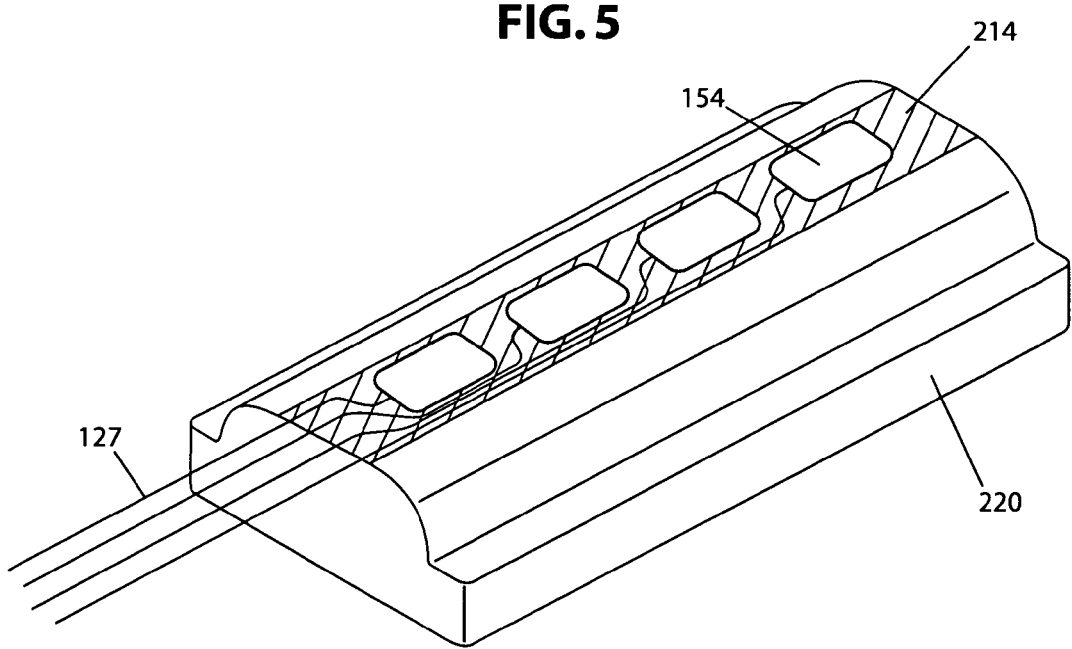
FIG. 5 is a schematic perspective view of one embodiment of a core with associated electrodes, according to the invention.

In one embodiment of the method of making an implantable microstimulator, a mounting material 214 is first placed on a core 220 as illustrated schematically in FIG. 5. The core 220 may be made of any material that can support the electrode(s) while a mold is being formed. Suitable materials for the core 220 include, but are not limited to, metals, polymers, plastics and ceramics. Preferably, the core 220 is made of a durable material that allows the core 220 to be reused. The core 220 can be made to resemble the shape of the implant. In one embodiment, at least one portion of the surface of the core 220 has a shape that is identical or similar to the shape of the microstimulator housing 102.

The mounting material 214 can be any material that enables the electrode(s) 154 to be positioned relatively stationary onto the core 220. Preferably, the mounting material 214 attaches non-permanently to the core 220. In one embodiment, the mounting material 214 is double sided adhesive tape or a vacuum sucking surface.

The electrode(s) 154 and conductor(s) 127 are then arranged on the mounting material 214 as illustrated schematically in FIG. 5. The electrode(s) 154 and conductor(s) 127 may be arranged in any pattern on the mounting material 214. If there is more than one electrode, preferably the electrodes 154 are arranged such that the electrodes 154 are equally spaced from each other. It will be recognized that the electrodes 154 may also be arranged on the mounting material 214 such that there is a non-uniform distance between the electrodes 154 to form a desired stimulation field pattern.

The conductor(s) 127 can be attached to the electrode(s) 154 by any method that allows the conductor(s) 127 to remain bonded to the electrode(s) 154 under expected implantation and usage conditions. For example, the conductor(s) 127 may be attached to the electrode(s) 154 by soldering, welding, diffusion bonding, laser welding, electrical resistance welding, and the like. The conductor(s) 127 may be attached to the electrode(s) 154 either before, during or after the electrode(s) 154 and conductor(s) 127 are positioned on the mounting material 214.

Figure 6:
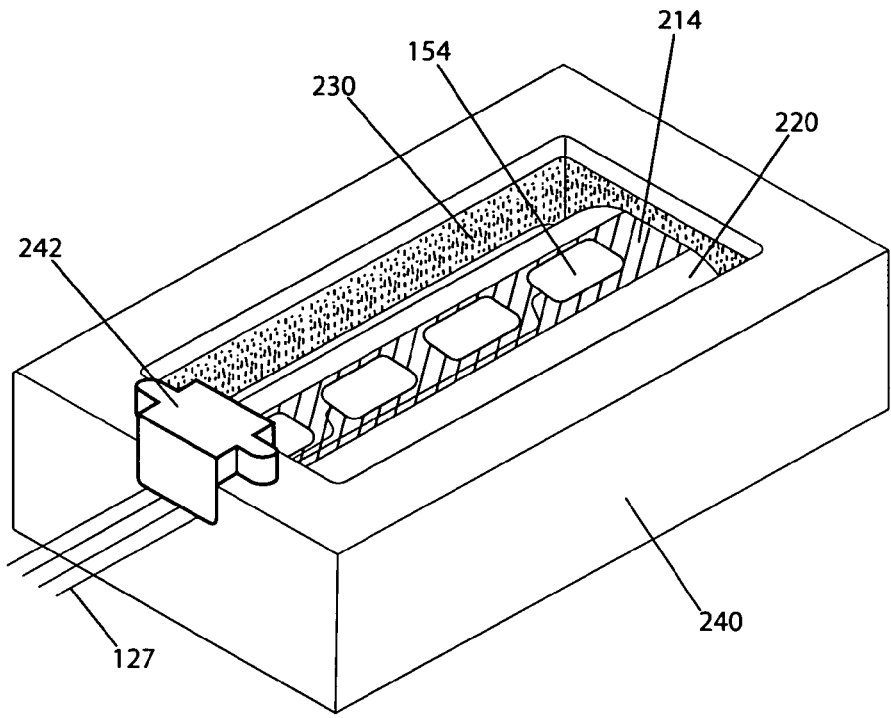
FIG. 6 is a schematic perspective view of the core of FIG. 5 disposed in a mold frame.

The arrangement of electrode(s) 154, conductor(s) 127, mounting material 214, and core 220 is then placed in a mold frame 240 as illustrated schematically in FIG. 6. A mold 230 may be formed, for example, by adding a material suitable for making the mold to the mold frame and allowing the material to harden, cure or otherwise solidify. For example, a liquid may be poured into the mold frame 240 and allowed to solidify (for example by cooling) or cure, thereby forming a mold 230 that can be separated from the core 220. In another embodiment, a liquid may be poured into the mold frame 240 and then polymerized or cross-linked into a solid by using a polymerizing or cross-linking agent. In another embodiment, a malleable solid may be pressed or formed into the mold frame 240 and allowed to solidify or cure, thereby forming a mold. The mold 230 can be made of any material that can be formed into a desired shape and that can be removed from the microstimulator housing 102. Suitable materials for the mold include, but are not limited to wax and polymers.

Figure 7:
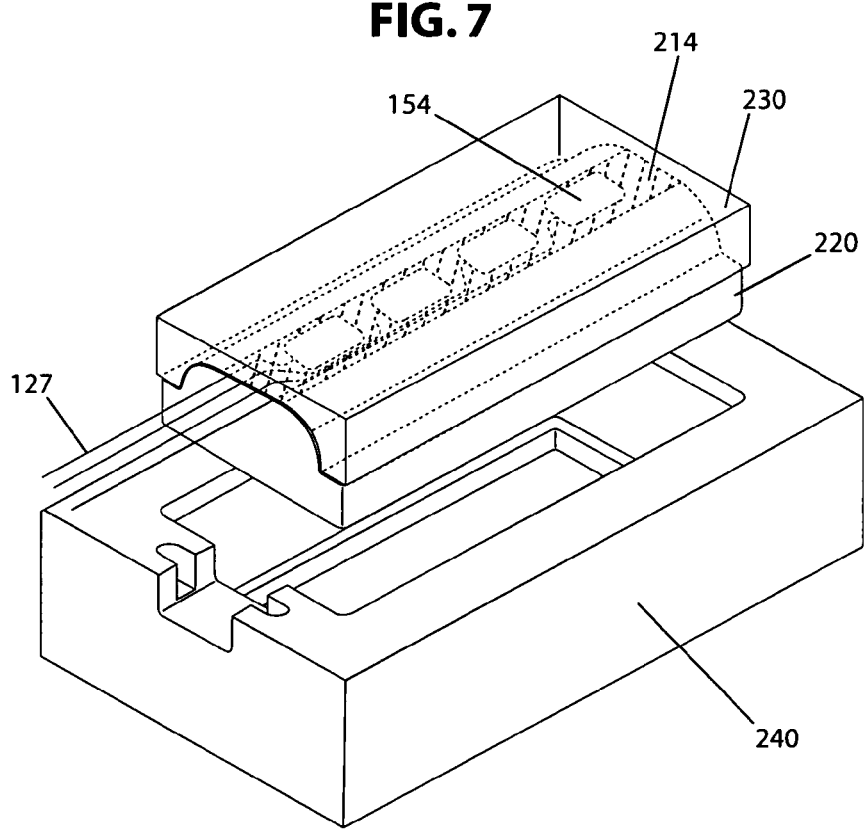
FIG. 7 is a schematic perspective view of the core of FIG. 5 and FIG. 6 after formation of a mold and removal of the core and the mold from the mold frame.
Figure 8:
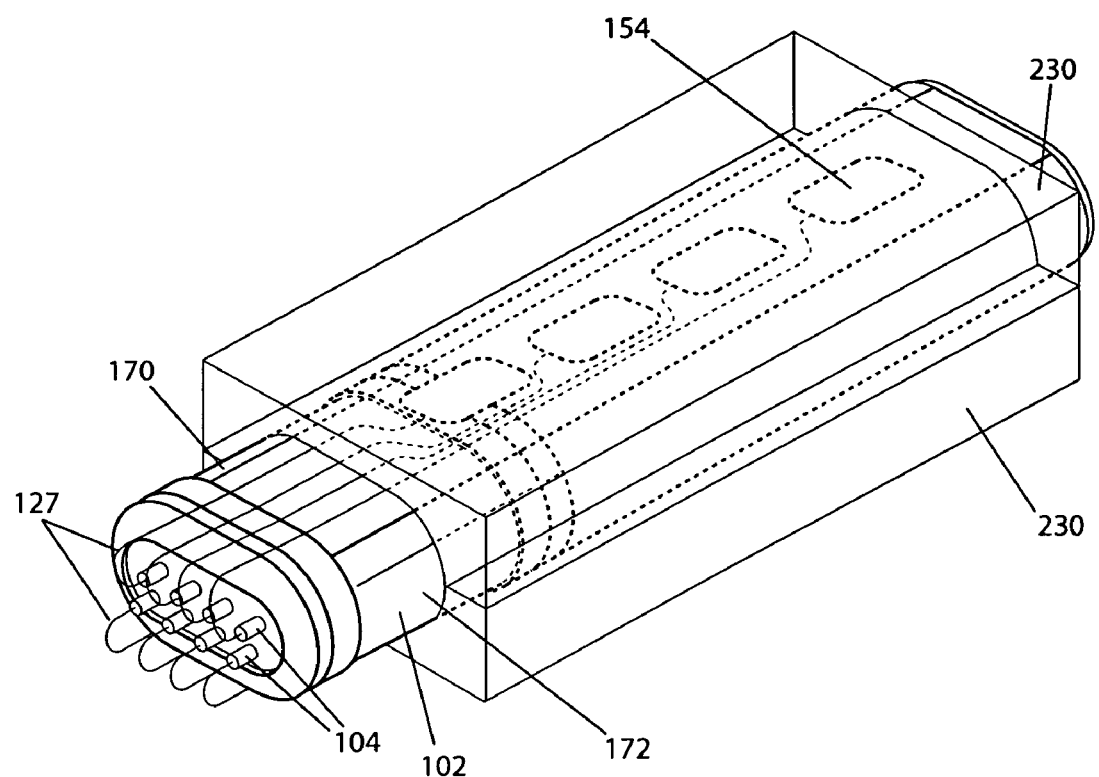
FIG. 8 is a schematic perspective view of one embodiment of two molds with associated electrodes disposed on opposite sides of the microstimulator housing, according to the invention.

Optionally, the core 220 and mold 230 with the electrode(s) 154 and conductor(s) 127 sandwiched between them may be removed from the mold frame 240 as illustrated in schematically FIG. 7. The core 220 and the mold 230 can then be separated such that the electrode(s) 154 and the conductor(s) 127 remain attached to the mold 230. The mounting material 214 is then removed from the electrode(s) 154 and conductor(s) 127. Adhesive 140 is then applied to the electrode(s) 154. The mold 230 with the electrode(s) 154 and conductor(s) 127 attached can next be disposed on the housing 102 of the microstimulator as illustrated schematically in FIG. 8. Optionally, another mold 230 with the electrode(s) 154 and conductor(s) 127 attached may be disposed on the opposite side of housing 102 as illustrated schematically in FIG. 8. Optionally, the adhesive may be cured to more securely bind the electrode(s) 154 to the housing 102.

The mold 230 is then removed from the housing 102 of the microstimulator in a manner that leaves the electrode(s) 154 and conductor(s) 127 attached to the housing 102 of the microstimulator. The mold 230 may be removed from the housing 102 of the microstimulator by any method that substantially removes the mold material and yet does not significantly alter the microstimulator components. In one embodiment, the mold 230 is removed by exposure to a solvent that dissolves the mold material. In another embodiment, the mold 230 is removed by exposure to heat. For example, the mold 230 can be made of wax and removed by exposure to acetone or by heating to melt the wax. The microstimulator with externally attached electrode(s) attached by an adhesive is illustrated schematically in FIG. 1. The conductor(s) 127 can then be connected to the conductive via(s) 104, for example, by laser welding, soldering, and resistance welding.

The microstimulator can be implanted into a patient and electrical signals can be provided to the conductive electrode(s) to stimulate at least one cell or tissue. The microstimulator can be implanted into the body tissue using a variety of methods including surgical methods. In some embodiments, the microstimulator can be implanted using a hypodermic needle or other insertion cannula. Examples of insertion techniques can be found in U.S. Pat. No. 6,051,017.

In at least some embodiments, electrodes 154 on only one side of the implantable microstimulator can be selected to provide stimulation of the desired tissues. This may provide more efficient stimulation of the tissues when compared to an implantable microstimulator with electrodes disposed on more than one side of the microstimulator or electrodes which provide roughly 360° stimulation from a portion (e.g., the tip) of the microstimulator.

The microstimulator electrodes may be selectively stimulated. In one embodiment, electrical signals are provided to the conductive electrodes 154 of the microstimulator simultaneously. In another embodiment, electrical signals are provided to the conductive electrode(s) 154 of the microstimulator independently of one another. Electrical signals can be provided to at least one, but not all of the conductive electrodes 154. Coordination of the electrical signals dispersed to the electrode(s) is often facilitated by a processor 204.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An implantable microstimulator, comprising:
a microstimulator housing comprising an exterior surface with a metal region, the housing defining an exterior and an interior;
a plurality of thin, flat, conductive electrodes each having an exposed broad active surface that is disposed over the metal region of the exterior surface of the housing;
non-conductive adhesive sandwiched between, and in direct contact with, the metal region and each of the plurality of conductive electrodes, the non-conductive adhesive attaching each of the plurality of conductive electrodes to a portion of the metal region with the non-conductive adhesive disposed on top of the exterior surface of the housing and beneath the exposed surface of each of the plurality of conductive electrodes;
an electronic subassembly disposed in the interior of the housing;
at least one conductive via extending from the interior of the housing to a location that is exterior to the housing, the at least one conductive via electrically coupled to the electronic subassembly; and
at least one exterior conductor that is disposed entirely external to the housing, the at least one exterior conductor electrically coupling the conductive via to the plurality of conductive electrodes, wherein at least a portion of the at least one exterior conductor is disposed external to the adhesive;
wherein the plurality of conductive electrodes are configured and arranged to stimulate tissue adjacent to the plurality of conductive electrodes on the housing of the microstimulator when implanted.

2. The implantable microstimulator of claim 1, wherein the at least one exterior conductor comprises a conductor wire.

3. The implantable microstimulator of claim 1, wherein a layer of adhesive between the plurality of conductive electrodes and the metal region of the housing is of a substantially uniform thickness.

4. The implantable microstimulator of claim 1, wherein the adhesive comprises a plurality of spacer particles.

5. The implantable microstimulator of claim 1, wherein the plurality of conductive electrodes are disposed on only one side of the housing.

6. The implantable microstimulator of claim 1, wherein the plurality of conductive electrodes are disposed on each of the at least two opposing sides of the housing.

7. The implantable microstimulator of claim 1, further comprising a battery.

8. The implantable microstimulator of claim 1, wherein the non-conductive adhesive is selected from the group consisting of: silicones, epoxies, and acrylics.

9. The implantable microstimulator of claim 1, wherein the length of the microstimulator is no greater than 30 mm and the lateral width of a side of the housing is no greater than 5 mm.

10. The implantable microstimulator of claim 1, wherein the exterior surface of the microstimulator housing comprises a non-conductive region, and wherein the at least one conductive via extends from the interior of the housing along the non-conductive region.

11. The implantable microstimulator of claim 1, wherein the broad active surfaces of each of the plurality of conductive electrodes are parallel to the metal region over which the adhesive is attached.

12. The implantable microstimulator of claim 4, wherein the plurality of spacer particles have uniform diameters.

13. The implantable microstimulator of claim 12, wherein the diameters of the plurality of spacer particles are equal to a thickness of the adhesive.

14. A method of making an implantable microstimulator, the method comprising:
   disposing an electronic subassembly in a microstimulator housing, the housing comprising an exterior surface with a metal region and defining an exterior and an interior;
   attaching a pluralilty of thin, flat, conductive electrodes each having an exposed broad active surface over the metal region of the exterior surface of the housing using a non-conductive adhesive sandwiched between, and in direct contact with, the metal region and each of the plurality of conductive electrodes, wherein the non-conductive adhesive is disposed on top of the exterior surface of the housing and beneath the exposed surface of each of the plurality of conductive electrodes;
   electrically coupling the electronic subassembly to at least one conductive via, wherein the conductive via extends from the interior of the housing to a location that is exterior to the housing; and
   electrically coupling the at least one conductive via to the plurality of conductive electrodes using at least one exterior conductor that is disposed entirely external to the housing, the at least one exterior conductor electrically coupling the conductive via to the plurality of conductive electrodes, wherein at least a portion of the at least one exterior conductor is disposed external to the adhesive;
   wherein the plurality of conductive electrodes are configured and arranged to stimulate tissue adjacent to the plurality of conductive electrodes on the housing of the microstimulator when implanted.

15. The method of making an implantable microstimulator of claim 14, wherein attaching a plurality of thin, flat, conductive electrodes each having an exposed broad active surface over the metal region of the exterior surface of the housing comprises attaching the plurality of conductive electrodes over the metal region of the housing using an adhesive comprising a plurality of spacer particles.

16. The method of making an implantable microstimulator of claim 14, wherein attaching a plurality of thin, flat, conductive electrodes each having an exposed broad active surface over the metal region of the exterior surface of the housing comprises attaching the plurality of conductive electrodes over the metal region of the housing using a layer of adhesive of a substantially uniform thickness.

17. The method of making an implantable microstimulator of claim 14, further comprising:
   disposing the plurality of conductive electrodes onto a mold; and
   applying adhesive to the plurality of conductive electrodes, wherein disposing the plurality of conductive electrodes onto a mold and applying adhesive to the plurality of conductive electrodes occur before attaching the plurality of conductive electrodes over the metal region of the housing using the adhesive.

18. The method of making an implantable microstimulator of claim 14, further comprising:
   disposing the plurality of conductive electrodes onto a core; and
   using the core to form a mold, onto which the plurality of conductive electrodes are transferred.

19. A method of using an implantable microstimulator, comprising:
   implanting an implantable microstimulator comprising a microstimulator housing having an exterior surface with a metal region, the housing defining an exterior and an interior; a plurality of thin, flat, conductive electrodes each having an exposed broad active surface that is disposed over the metal region of the exterior surface of the housing; non-conductive adhesive sandwiched between, and in direct contact with, the metal region and each of the plurality of conductive electrodes, the non-conductive adhesive attaching each of the plurality of conductive electrodes to a portion of the metal region with the non-conductive adhesive disposed on top of the exterior surface of the housing and beneath the exposed surface of each of the plurality of conductive electrodes; an electronic subassembly disposed in the interior of the housing; at least one conductive via extending from the interior of the housing to a location that is exterior to the housing, the at least one conductive via electrically coupled to the electronic subassembly; and at least one exterior conductor that is disposed entirely external to the housing, the at least one exterior conductor electrically coupling the conductive via to the plurality of conductive electrodes, wherein at least a portion of the at least one exterior conductor is disposed external to the adhesive; and
   providing an electrical signal to the plurality of conductive electrodes to stimulate a tissue adjacent to the plurality of conductive electrodes on the housing of the microstimulator.

20. The method of claim 19, wherein providing an electrical signal to the plurality of conductive electrodes to stimulate a tissue comprises providing the electrical signal independently to each of the plurality of conductive electrodes.

* * * * *